United States Patent [19]
Mushika

[11] Patent Number: 5,217,430
[45] Date of Patent: * Jun. 8, 1993

[54] APPARATUS FOR DRIVING A MEDICAL APPLIANCE

[75] Inventor: Sadahiko Mushika, Aichi, Japan

[73] Assignee: Aisin Seiki K.K., Kariya, Japan

[*] Notice: The portion of the term of this patent subsequent to Jul. 24, 2007 has been disclaimed.

[21] Appl. No.: 816,541

[22] Filed: Dec. 30, 1991

Related U.S. Application Data

[63] Continuation of Ser. No. 330,675, Mar. 30, 1989, abandoned.

[30] Foreign Application Priority Data

Mar. 30, 1988 [JP] Japan .................................. 63-77482

[51] Int. Cl.$^5$ ........................................... A61N 1/362
[52] U.S. Cl. ......................................... 600/18; 623/3
[58] Field of Search ................................ 600/16-18; 128/752; 604/99; 623/3

[56] References Cited

U.S. PATENT DOCUMENTS

| | | | |
|---|---|---|---|
| 4,556,997 | 12/1985 | Takamiya et al. | 600/16 |
| 4,583,525 | 4/1986 | Suzuki et al. | 600/16 |
| 4,648,385 | 3/1987 | Oumi et al. | 600/17 |
| 4,787,368 | 11/1988 | Kageyama | 600/18 |
| 4,794,910 | 1/1989 | Mushika | 600/18 |
| 4,796,606 | 1/1989 | Mushika | 600/18 |
| 4,832,005 | 5/1989 | Takamiya et al. | 600/18 |
| 4,942,735 | 7/1990 | Mushika et al. | 600/16 |

Primary Examiner—Kyle L. Howell
Assistant Examiner—John P. Lacyk
Attorney, Agent, or Firm—Sughrue, Mion, Zinn, Macpeak & Seas

[57] ABSTRACT

Apparatus for driving a medical appliance has a single compressor for generating both the positive and the negative pressures. Positive and negative pressure valves for controlling communication with the atmosphere are connected to the outlet and inlet terminals of the compressor and the outlet and inlet terminals of the compressor are also connected to a positive pressure accumulator and a negative pressure accumulator, respectively. The apparatus has pressure sensors to sense when the pressures in the accumulators reach a set pressure. The apparatus further has a one-way valve in the positive pressure line between the compressor and the valve or in the negative pressure line between the compressor and the valve. The apparatus prohibits the positive and negative pressure valves from being open at the same time.

2 Claims, 4 Drawing Sheets

APPARATUS FOR DRIVING A MEDICAL APPLIANCE

This is a continuation of application Ser. No. 07/330,675 filed Mar. 30, 1989, now abandoned.

BACKGROUND OF THE INVENTION

The present invention relates to an apparatus for driving a medical appliance such as an artificial heart or balloon pump in an artery, and more particularly, to a fluid driving apparatus for changing a positive and negative fluid pressure.

A conventional driving apparatus for a medical appliance is shown in, for example, Japanese Kokai Application No. 61(1986)-129500. In this conventional apparatus, the inlet terminal of the compressor is used for a negative pressure source and the outlet terminal of the compressor is used for a positive pressure source. Thus, this apparatus does not have a separate vacuum pump for negative pressure. This apparatus also has a valve 18 which connects the outlet terminal of the compressor to the atmosphere and a valve 19 which connects the inlet terminal of the compressor to the atmosphere. This apparatus controls valves 18 and 19 as follows:
1) positive pressure mode if,
   a) pressure of the positive accumulator < Ps1: 18 close, 19 open
   b) pressure of the negative accumulator > Vs2: 18 open, 19 close
   c) not a) or b): 18 open, 19 open
2) negative pressure mode if,
   d) pressure of the negative accumulator ≥ Vs1:18 open, 19 close
   e) pressure of the positive accumulator Ps2:18 close, 19 open
   f) not d) or e):18 open, 19 open wherein, Ps1, Ps2, Vs1 and Vs2 are set values.

In this apparatus, when it is in a positive pressure mode, positive pressure regulation has priority and when it is in a negative pressure mode, negative pressure regulation has priority. The set values are different in each mode.

However, this apparatus has a loss of generated pressure because the compressor has to be operated often in the idle mode which is the above mentioned cases c) and f). This makes the compressor big in size. In addition to this loss in this apparatus, the priority of the pressure regulations is changed in response to the pressure changes between positive and negative so that the valve 18 or valve 19 connects the compressor to the atmosphere. Because the compressor is connected to the positive and negative pressure accumulators by relatively large diameter pipes, when the valve 18 or valve 19 is opened, the pressures in the pipes are exhausted to the atmosphere. This makes for a loss of generated pressures which are increased when the changing frequency of positive and negative pressures is increased. Furthermore, this apparatus makes undesirable noise because of these drawbacks.

SUMMARY OF THE INVENTION

Accordingly, one of the objects of the present invention is to produce a driving apparatus for a medical appliance to obviate the above drawbacks by generating both positive and negative pressure by using a single compressor and eliminating the loss of generated pressures.

Another object of the present invention is to produce a driving apparatus for a medical appliance to reduce the noise of the compressor. A further object of the present invention is to produce a driving apparatus for a medical appliance which in reduced in size.

To achieve the above objects, and in accordance with the principles of the invention as embodied and broadly described herein, an apparatus for driving a medical appliance comprises a compressor means for generating a negative pressure at an inlet terminal and a positive pressure at an outlet terminal a positive pressure accumulating means connected to said outlet terminal of said compressor means;

a negative pressure accumulating means connected to said inlet terminal of said compressor means;

connecting means for connecting said positive and negative pressure accumulating means to said medical appliance; a switch vale means connected to said positive and negative pressure accumulating means for selectively applying a pressure to said connecting means;

a positive pressure valve means connected between said outlet terminal of said compressor means and said positive pressure accumulating means;

a negative pressure valve means connected between said inlet terminal of said compressor means and said negative pressure accumulating means;

a positive pressure sensing means for detecting a pressure between said outlet terminal of said compressor means and said switching valve means;

a negative pressure sensing means for detecting a pressure between said inlet terminal of said compressor means and said switching valve means; and electronic control means for opening and closing said switching valve means in accordance with predetermined timings, for opening and closing said positive and negative pressure valve means in accordance with both positive and negative pressure set values provided in said electronic control means and output signals from said positive and negative pressure sensing means and for prohibiting one of said positive and negative pressure valve means from opening when the other positive or negative pressure valve means is opened.

In accordance with the above mentioned apparatus of this invention, the state wherein both the positive and negative pressure valves are opened is prohibited. Thus, the inlet and outlet terminals of the compressor are not open to the atmosphere at the same time. Since at least one of the positive and negative valves is closed, some load is applied to the compressor and an idle operation of the compressor is prevented as well as preventing pressure losses from the inlet and outlet terminals of the compressor. Therefore, the size and the noise of the compressor can be reduced.

In a preferred embodiment of the present invention, the apparatus has a one-way valve connected between the compressor and the positive pressure accumulator or between the compressor and the negative pressure accumulator and the electronic control means controls pressure regulation in the line to which the one-way valve is not connected, prior to pressure regulation in the other line to which the one-way valve is connected. For example, when the negative pressure valve is controlled prior to the positive pressure, the negative pressure valve means is opened only if the pressure between the negative pressure accumulator and the compressor is lower than the set value. Then the generated negative pressure is not exhausted to the atmosphere. In this embodiment, it is better to place the negative pressure sensing means closer to the negative pressure valve means.

BRIEF DESCRIPTION OF THE DRAWINGS

For a full understanding of the true scope of the invention, the following detailed description should be read in conjunction with the drawings, wherein.

DETAILED DESCRIPTION OF THE PREFERRED EMBODIMENTS

In the following, preferred embodiments of the present invention will be described with reference to the drawings.

Figure 2:
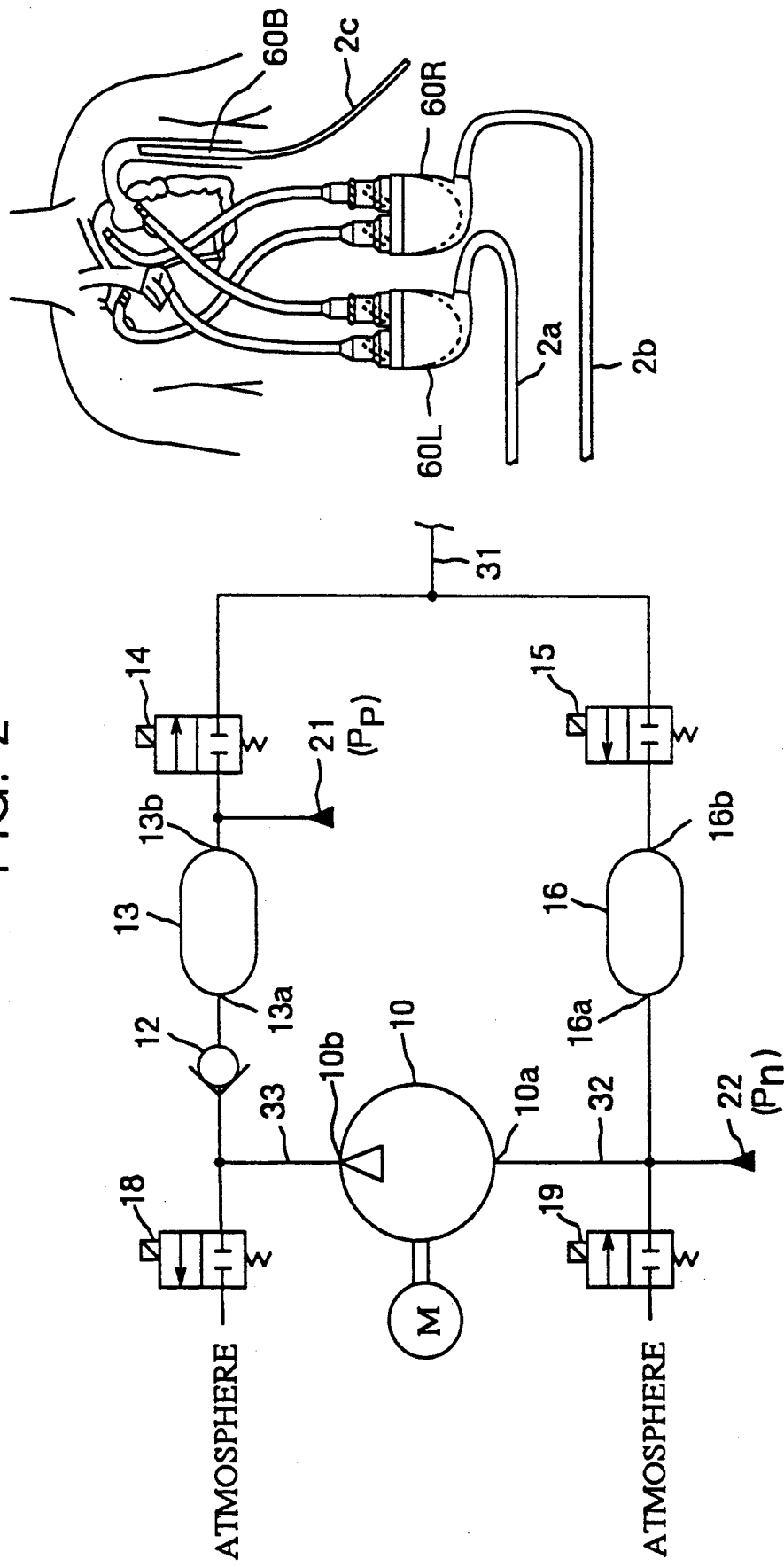
FIG. 2 is a block diagram showing the system configuration of the driving apparatus of this invention.

FIG. 2 illustrates one embodiment of a driving apparatus of the present invention. Referring to FIG. 2, artificial hearts are designated at 60L and 60R and a balloon pump is designated at 60B. This type of artificial heart is called an assistance type artificial heart because it is used for assistance of a natural heart or temporarily used as a substitute heart. An artificial heart has a blood chamber and a driving chamber separated by a flexible diaphragm and has valves at the inlet and outlet of the blood chamber. The diaphragm is driven periodically by applying a pulsatile fluid to the driving chamber so that the blood is pumped from the inlet to the outlet of the blood chamber. Tubes 2a and 2b are connected to the driving chambers of the artificial hearts 60L and 60R, respectively.

Tube 2c is connected to the balloon pump 60B. In this embodiment, each of the tubes 2a, 2b and 2c is connected to the output 31 of the driving apparatus.

A compressor 10 is driven by a motor M. In this embodiment, the compressor 10 is driven all the time and does not stop. An inlet terminal 10a of the compressor 10 is connected to a negative pressure line 32 and an outlet terminal 10b is connected to a positive pressure line 33. Another end of the negative pressure line 32 is connected to an inlet terminal 16a of a negative pressure accumulator 16. The negative pressure line 32 is also connected to a pressure sensor 22 and an outlet terminal of an electric solenoid valve 19. The inlet terminal of the solenoid valve 19 is opened to the atmosphere. An outlet terminal of the negative pressure accumulator 16 is connected to an inlet terminal of a switching solenoid valve 15.

Another end of the positive pressure line 33 is connected to an inlet terminal 13a of a positive pressure accumulator 13. At the positive pressure line between the compressor 10 and the positive pressure accumulator 13, a one-way valve 12 is inserted. An inlet terminal of the positive pressure solenoid valve 18 is connected to the pressure line between the compressor 10 and the one-way valve 12. The outlet terminal of the solenoid valve 18 is opened to the atmosphere. An outlet terminal of the positive pressure accumulator 13 is connected to an inlet terminal of a switching solenoid valve 14. A pressure sensor 21 is connected to the line between the outlet terminal 13b of the positive pressure accumulator 13 and an inlet terminal of the switching solenoid valve 14. The outlet terminals of the switching solenoid valves 14 and 15 are connected to the output terminal 31.

The operation of the fluid circuit will be explained briefly. The inlet terminal 10a and the outlet terminal 10b of the compressor 10 supply negative and positive pressures, respectively. The negative pressure is accumulated in the negative accumulator 16 and the positive pressure is accumulated in the positive accumulator 13. If a pressure in the negative accumulator 16 becomes excessive, the valve 19 is opened to keep the pressure constant. If a pressure in the positive accumulator 13 becomes excessive, the valve 18 is opened to keep the pressure constant. However, the valves 18 and 19 are not opened at the same time. The switching valves 14 and 15 are switched open and closed in accordance with a natural heart beat and supply positive and negative pressures to the output terminal 31 periodically.

Figure 3:
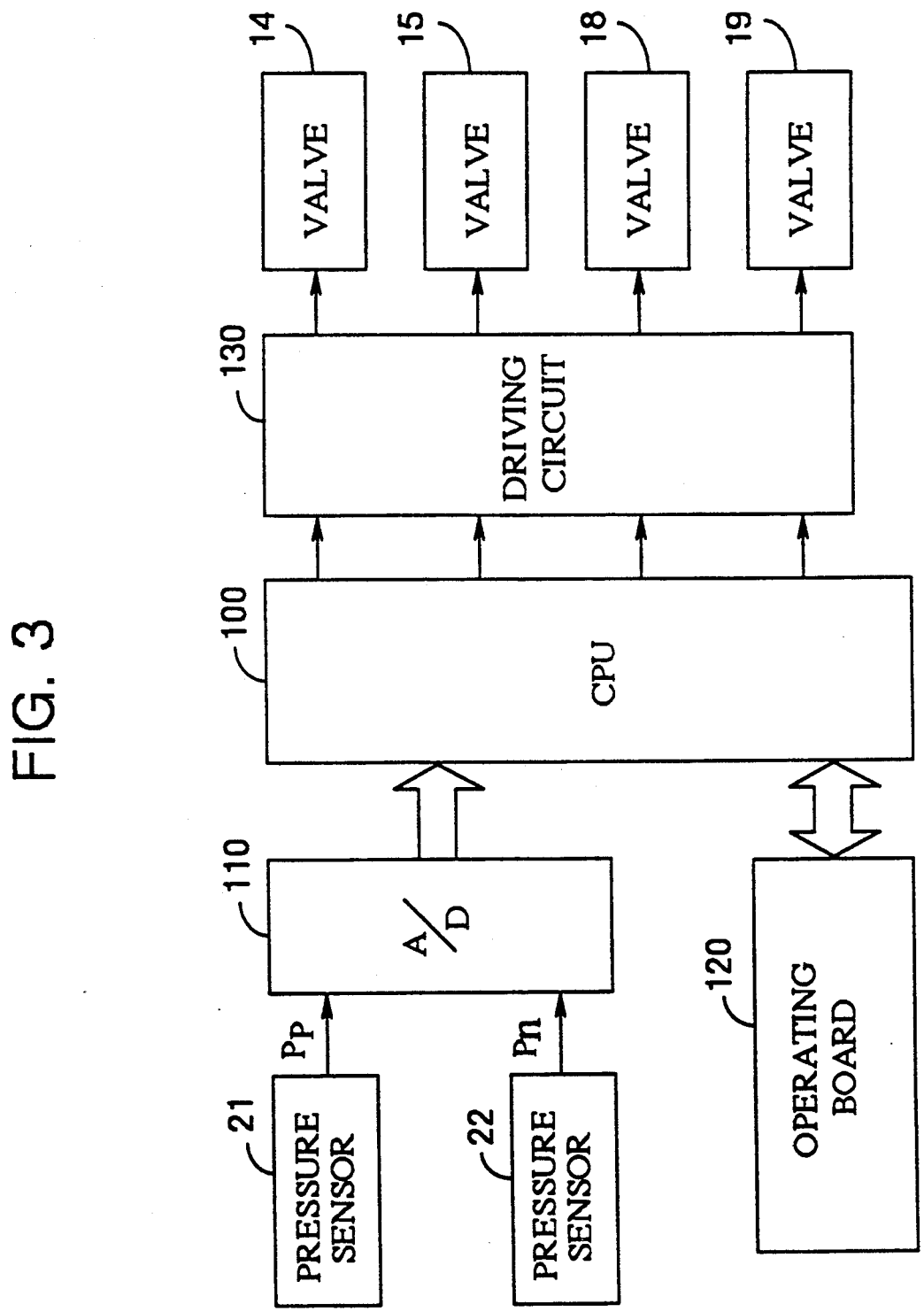
FIG. 3 is a circuit diagram showing the circuitry of the electronic control means of this invention.

FIG. 3 shows a circuit diagram showing the circuitry of the electronic control means.

Referring to FIG. 3, the circuit has a microprocessor 100. Input and output ports of the microprocessor 100 are connected to A/D conversion circuit 110, operating board 120 and driving circuit 130. The pressure sensors 21 and 22 output analog electric signals to A/D conversion circuit 110. The A/D conversion circuit 110 samples and converts these signals into digital signals for supply to the microprocessor 100. The driving circuit 130 is connected to the electric valves 14, 15, 18 and 19. The operating board 120 has key switches to input driving parameters and a display to show the parameters (not shown). The parameters include set pressures for positive and negative pressures Psp and Psn, duration D for applying a positive pressure, duration R for applying a negative pressure, heart beat period, etc.

Figure 1:
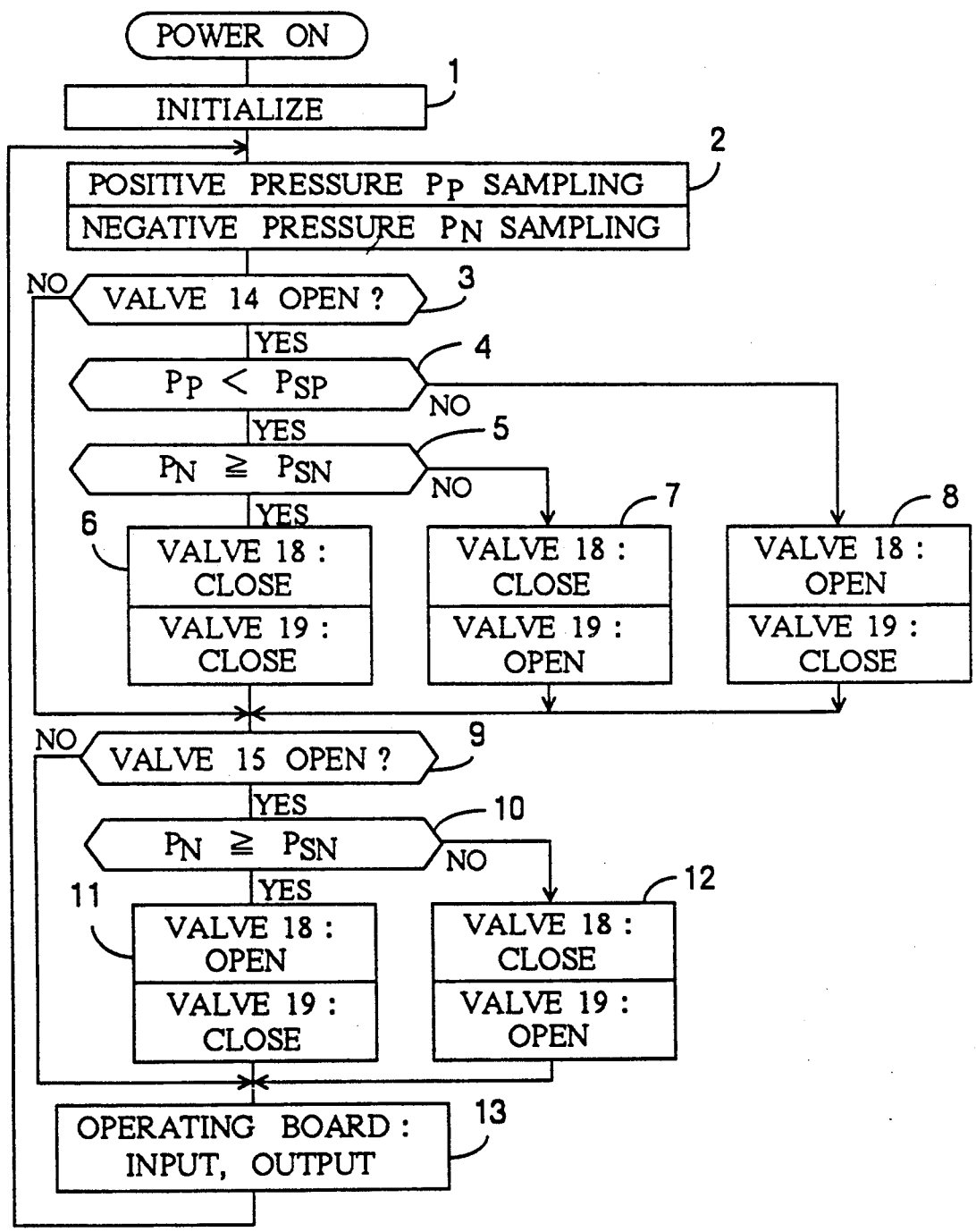
FIGS. 1 and 4 are flow charts showing the operation of the electronic control means of this invention as shown in FIG. 3.
Figure 4:
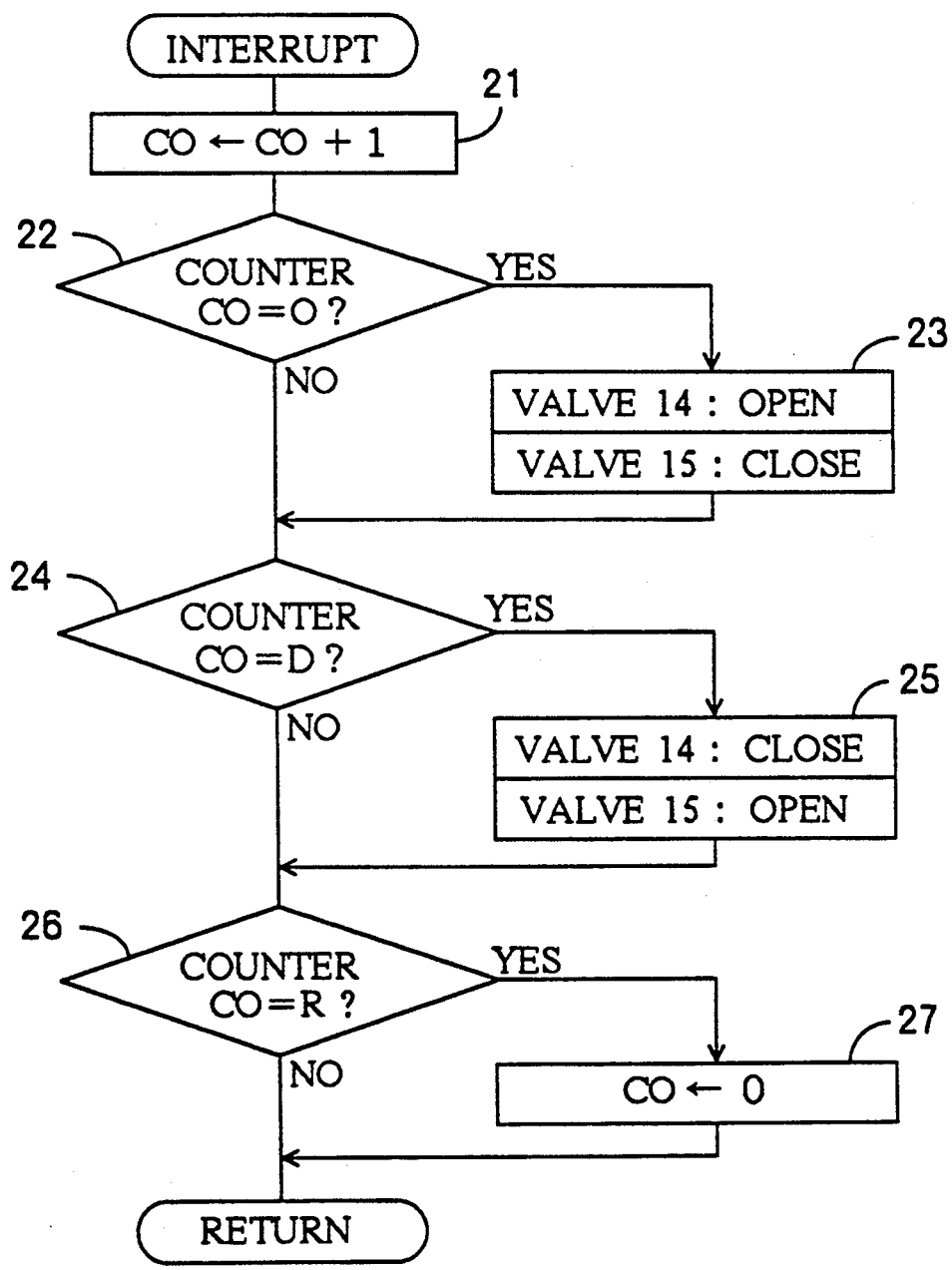

FIGS. 1 and 4 are flow charts showing the schematic operation of the microprocessor 100. FIG. 1 shows a main routine and FIG. 4 shows an interrupt processing routine. The interruption is made in a short time period counted by a timer in the microprocessor 100.

Referring to FIG. 1, when the power is on the parameters are initialized to clear memory and output signals and set the predetermined parameters in the memory as initial values. In step 2, the control for controlling the A/D converter 110 samples and converts the positive pressure signal of the sensor 21 and the negative pressure signal of the sensor 22 into digital positive and negative pressure signals Pp and Pn, respectively. In step 3, the control judges whether the switching valve 14 is open. If the valve 14 is opened, that is the positive pressure mode, the control goes to step 4 and if the valve 14 is not opened, that is the negative pressure mode, the control goes to step 9. In step 4, the sampled positive pressure Pp is compared with the positive set pressure Psp. If the pressure Pp is equal or greater than the pressure Psp, that is the detected pressure is greater than the set pressure, the valve 18 is opened and the valve 19 is closed in step 8. The compressor 10 operates to reduce the negative pressure in the negative pressure accumulator 16 and the line 32. Compressed air generated by the compressor 10 is exhausted to the atmosphere through the valve 18. At this time, the pressure in the line 33 is lowered to the atmosphere level, however, a pressure in the positive pressure accumulator 13 is prevented from decreasing by the one-way valve 12. In step 4, if the detected pressure Pp is smaller than the set pressure Psp, the detected negative pressure Pn is compared with the negative set pressure Psn in step 5. If the detected pressure Pn (absolute value) is smaller than the set pressure Psna (absolute value), that is, the detected pressure is in excess of the set pressure, the valve 18 is closed and the valve 19 is opened in step 7. The air is supplied to the inlet terminal 10a of the compressor 10 through the valve 19 and the negative pressure in the negative pressure accumulator 16 and the line 32 is lowered. A pressure in the positive pressure accumulator 13 is increased because the pressure of the compressor 10 is supplied through the one-way valve 12. In step 5, if the detected, pressure Pna is equal or greater than the set pressure Psna, that is, the detected pressure is lower than the set pressure, the valves 18 and 19 are closed in step 6. The compressor 10 decreases the pressure in the negative pressure accumulator 16 and the line 32 and increases the pressure in the positive pressure accumulator 13 and the line 33.

In step 9, the control judges whether the switching valve 15 is open. If the valve 15 is open, that is, the negative pressure mode, the control goes to step 10 and if the valve 15 is not opened, that is, the positive pressure mode, the control goes to step 13. In step 10, the sampled negative pressure Pna is compared with the negative set pressure Psn. If the pressure Pn is smaller than the pressure Psna, that is, the detected pressure is greater than the set pressure, the valve 18 is closed and the valve 19 is opened in step 12. The compressor 10 operates to reduce the negative pressure in the negative pressure accumulator 16 and the line 32. The air is supplied through the valve 19 to the compressor 10. At this time pressurized air from the compressor 10 is supplied to the positive pressure accumulator 13 through the one-way valve 12 so that the pressure in the accumulator 13 is increased. In step 10, if the detected pressure Pna is equal or greater than the set pressure Psna, that is, the detected negative pressure is lower than the set pressure, the control goes to step 11. The valve 18 is opened and the valve 19 is closed. The compressor 10 operates to increase the pressure in the negative pressure accumulator 16 and the line 32. The compressed air generated by the compressor 10 is exhausted to the atmosphere through the valve 18. At this time, the pressure in the line 33 is lowered to the atmosphere level; however, the pressure in the positive pressure accumulator 13 is prevented from decreasing because of the one-way valve 12.

In step 13, the control reads the key inputs from the operating board 120, changes the parameters and controls the display.

Referring to FIG. 4, an interrupt processing routine is explained, a counter counts up one if the interrupt processing routine is executed in step 21. This interrupt processing routine is executed in a short period of time periodically. In steps 22, 24 and 26, the value of the counter is checked. When the value of the counter shows "0", the control goes to step 23. The valve 14 is opened and the valve 15 is closed so that the output pressure is changed from the negative into the positive. When the value of the counter shows "D", the control goes to step 25. The valve 14 is closed and the valve 15 is opened so that the output pressure is changed from the positive into the negative. When the value of the counter shows "R", the control clears the counter to "0".

The above described embodiment has a priority for the negative pressure regulation. In the same way, it is also possible to provide an embodiment which has a priority for the positive pressure regulation. In that case, the one-way valve 12 is removed from the line 33 and placed in the line 32. It is preferable that the sensor 21 is relocated to line 33 and the sensor 22 is relocated to the line between the negative pressure accumulator 16 and the valve 15.

The invention has been described in an illustrative manner and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. An apparatus for driving a medical appliance consisting essentially of:

a compressor means for generating a negative pressure at an inlet terminal and a positive pressure at an outlet terminal;

a positive pressure accumulating means for accumulating fluid under positive pressure connected to said outlet terminal of said compressor means;

a negative pressure accumulating means for accumulating fluid under negative pressure connected to said inlet terminal of said compressor means;

a connecting means adapted to connect said medical appliance to said positive and negative pressure accumulating means;

switching valve means connected to said positive and negative pressure accumulating means for selectively applying a pressure to said connecting means;

positive pressure valve means for controlling positive pressure connected between said outlet terminal of said compressor means and said positive pressure accumulating means;

negative pressure valve means for controlling negative pressure connected between said inlet terminal of said compressor means and said negative pressure accumulating means;

positive pressure sensing means connected between said outlet terminal of said compressor means and said switching valve means for detecting positive pressure;

negative pressure sensing means connected between said inlet terminal of said compressor means and said switching valve means for detecting negative pressure;

a single one-way valve means connected between said compressor means and only one of said positive and negative pressure accumulating means for permitting flow only in one direction between said compressor and said only one of said positive and negative pressure accumulating means;

operating means for providing operating parameters including predetermined timings and positive and negative pressure set values; and electronic control means connected to said switching valve means and said positive and negative pressure valve means, said sensing means and said operating means for receiving said parameters for opening and closing said switching valve means in accordance with said predetermined timings, for opening and closing said positive and negative pressure valve means in accordance with both said positive and negative pressure set values provided by said operating means to said electronic control means and output signals from said positive and negative pressure sensing means and for prohibiting one of said positive and negative pressure valve means from opening when the other positive or negative pressure valve means is opened.

2. As apparatus as set forth in claim 1, wherein said one-way valve means is connected between said compressor and said positive pressure accumulating means for allowing fluid flow only to said positive pressure accumulator and wherein said electronic control valve means controls the pressure between said compressor and said negative pressure accumulator.

* * * * *